United States Patent [19]
Greed, Jr.

[11] Patent Number: 5,453,830
[45] Date of Patent: Sep. 26, 1995

[54] SPATIALLY ISOLATED DIFFRACTOR ON A CALIBRATION SUBSTRATE FOR A PELLICLE INSPECTION SYSTEM

[75] Inventor: James J. Greed, Jr., Los Gatos, Calif.

[73] Assignee: VLSI Standards, Inc., San Jose, Calif.

[21] Appl. No.: 259,562

[22] Filed: Jun. 14, 1994

Related U.S. Application Data

[63] Continuation of Ser. No. 901,119, Jun. 19, 1992.

[51] Int. Cl.⁶ .............................. G01J 1/02; G01N 21/88
[52] U.S. Cl. ............................................................. 356/243
[58] Field of Search ................................... 356/243, 237

[56]        References Cited
        U.S. PATENT DOCUMENTS

| | | | |
|---|---|---|---|
| 4,386,850 | 6/1983 | Leahy | 356/243 |
| 4,468,120 | 8/1984 | Tanimoto et al. | 356/237 |
| 4,512,659 | 4/1985 | Galbraith et al. | 356/243 |
| 4,610,541 | 9/1986 | Tanimoto et al. | 356/237 |
| 4,636,073 | 1/1987 | Williams | 356/243 |
| 4,767,660 | 8/1988 | Hosoda et al. | 428/209 |
| 4,889,998 | 12/1989 | Hayano et al. | 250/563 |
| 4,966,457 | 10/1990 | Hayano et al. | 356/237 |

OTHER PUBLICATIONS

Gaston, C. A., "Standard Wafer for Intensity and Focus Testing," *IBM Technical Disclosure Bulletin*, vol. 24, No. 11A, Apr. 1982.

*Primary Examiner*—Vincent P. McGraw
*Assistant Examiner*—K. P. Hantis
*Attorney, Agent, or Firm*—Schneck & McHugh

[57]        ABSTRACT

A test device for calibrating an optical surface inspection system, such as a pellicle or reticle inspection system, comprising a substrate having raised diffractors with at least one beam-diffracting geometric feature aligned to diffract light directed from an angle of incidence of less than 30°. The beam-diffracting geometric feature is preferably a vertex aligned generally perpendicular to the surface of the substrate. A detection beam which impinges the vertex is diffracted, with diffracted beams being collected by a collector. The raised diffractor thereby simulates a foreign particle on a substrate, allowing calibration of the system. The apparent size of the diffractor and therefore the simulated particle can be varied by varying the vertices or the height of the raised diffractor. If a substrate is to have more than one diffractor, the diffractor should be spaced apart by a distance greater than the diameter of the detection beam.

16 Claims, 2 Drawing Sheets

SPATIALLY ISOLATED DIFFRACTOR ON A CALIBRATION SUBSTRATE FOR A PELLICLE INSPECTION SYSTEM

This is a continuation of copending application Ser. No. 07/901,119 filed on Jun. 19, 1992.

TECHNICAL FIELD

The present invention relates generally to devices for calibrating optical surface inspection systems and more particularly to devices for calibrating a pellicle inspection system.

BACKGROUND ART

Optical inspection systems for detecting particles on the surface of a semiconductor substrate and for measuring surface roughness of a semiconductor wafer are well known. Typically, a detection beam is scanned across the surface of a wafer and a collector is used to collect light from the semiconductor substrate. The detector beam is directed at a 90° angle relative to the semiconductor surface under test. A smooth surface provides a predictable intensity of reflected light from the surface. However, surface roughness and foreign matter cause a scattering of the radiation and a change in the light that is received at the collector.

Optical inspection systems for semiconductor wafers must be tested and should be periodically calibrated to ensure uniformity of system sensitivity over time. A device and a method for calibrating a system used in determining surface roughness and detecting foreign matter on a semiconductor wafer are described in U.S. Pat. No. 4,512,659 to Galbraith et al. A beam is projected onto a surface having arrays of artificial defects. The artificial defects may take the form of a pit in the surface or a raised mesa on the surface. The artificial defects scatter the incident light, thereby simulating pits and raised areas on a semiconductor wafer. The spacing between artificial defects is less than the diameter of the incident beam. The surface having the array of artificial defects can be used as a reference device whenever an inspection system requires recalibration.

In addition to the use of optical inspection systems for determining surface roughness and foreign matter on a semiconductor wafer, such systems are used in determining the presence and location of particles on a masking device employed in photolithographically fabricating integrated circuits on the semiconductor wafer. Masking devices are herein defined to include reticles and pellicles. A pellicle is a thin transparent film that is spaced apart from a reticle or the like. Any particles that would otherwise come to rest on the surface of a reticle are instead seated on the pellicle. The particles can then be maintained outside of the focal plane of the apparatus used in transferring the pattern on a reticle to a semiconductor wafer.

There are a number of differences between optical inspection systems for semiconductor wafers and systems for inspecting a reticle or pellicle. In wafer inspection, the angle of incidence of an incident beam is often approximately 90° to the wafer. Pellicle inspection is typically associated with a grazing incidence angle, i.e., one in which the detection beam is nearly parallel to the pellicle surface. Thus, particles on a pellicle can cause "vignetting," or shadowing, of other particles. Vignetting can be a result of a first particle being directly behind a second particle with respect to the angle of incidence of the detection beam or with respect to light that would otherwise reach a collector after being scattered by the second particle.

An object of the present invention is to provide a test device for calibrating an optical surface inspection system in which the angle of incidence of the detection beam is less than 30°, wherein the test device is less susceptible to vignetting and is easily manufactured, handled and cleaned.

SUMMARY OF THE INVENTION

The above object has been met by a test device having a planar surface with at least one raised area that includes a beam-diffracting geometric feature that ensures an unimpeded path from a detector beam source to the raised area and from the raised area to a detector. The position of the raised area and the configuration of the beam-diffracting geometric feature are such that vignetting does not jeopardize calibration even when the angle of incidence of a detection beam is one degree relative to the planar surface and when the surface includes an array of raised areas. In a preferred embodiment, the beam-diffracting geometric feature is a vertex that is generally perpendicular to the planar surface of the test device.

The test device is a substrate having the optical characteristics of a pellicle, but having a thickness greater than that of a pellicle so that the test device can withstand the stresses of handling and cleaning. For example, the substrate may be made of a thin glass. The raised areas are single-body diffractors that are lithographically formed. The geometric properties of the diffractors may be varied to simulate foreign particles of different sizes. The number of vertices of a diffractor, the height of the diffractor, and the lateral dimension of the diffractor determine the apparent size of the raised area, as viewed by the detector.

The present invention is particularly suited for calibrating systems in which an incident beam has an angle of incidence of less than 30°, such as systems used for inspecting pellicles. The pellicle-simulating substrate may be connected to a reticle and inserted into the system in a position which places the surface having the diffractors within the extrafocal plane of a pellicle. The diffractors are spaced apart by a distance greater than the diameter of the detection beam. This is in contrast to calibration devices for semiconductor wafer inspection systems in which the angle of incidence is approximately 90° and in which any raised areas on a calibration device are spaced apart by a distance less than the diameter of the detection beam.

An advantage of the present invention is that the geometries of the raised diffractors allow a diffraction of light with an efficiency adequate to ensure detection. That is, the vertices direct radiation so that a greater percentage of the light is received by a detector. Another advantage is that the number of vertices, the height, and the lateral dimension of the diffractors can be varied to simulate particles of various sizes. The raised diffractors are formed using conventional microlithographic printing techniques, such as etching portions of the surface of a glass substrate. The test device is made of a material that has a sufficient thickness to allow handling of the device without any concern for fragility that would typically be associated with a substrate designed to simulate a thin pellicle.

BEST MODE FOR CARRYING OUT THE INVENTION

Figure 1:
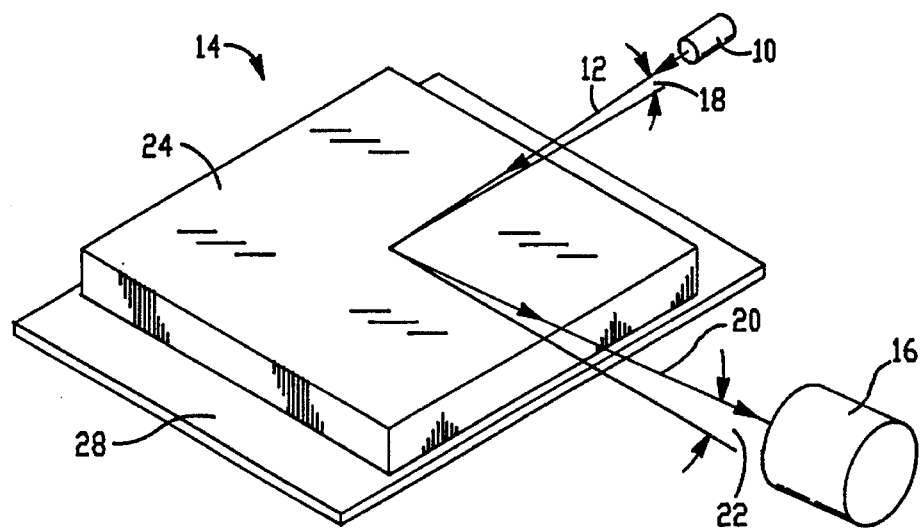
FIG. 1 is a perspective view of a pellicle inspection system shown in operation with a test device in accord with the present invention.

With reference to FIG. 1, a source 10 of a laser beam having an optical axis 12 is shown directing a detection beam at a test device 14. Typically, the detection beam is caused to scan the surface of the test device. The scanning can occur by redirecting the detection beam or by moving the test device along x, y and z axes. Apparatus for achieving proper movement of the test device is known in the art.

While the test device 14 will be described and illustrated as being used for calibrating a pellicle inspection system that includes the laser source 10 and a collector 16, the present invention may be used with other systems in which a detection beam is directed at a grazing angle of incidence relative to a surface to be inspected. Pellicle inspection systems may be associated with an incidence angle of 1°±0.5°, but this incidence angle may be as great as 30° relative to the upper surface of the test device 14. A raised area on the upper surface that is along the optical axis 12 will cause radiation 20 to be directed at the collector 16. The angle 22 of the collector relative to the upper surface of the test device may be 5°. Only a fraction of the detection beam that strikes a raised area is received at the collector. Yet, a pellicle inspection system should be one that allows a user to determine particle size, particle count and the coordinate location of particles. To ensure repeatability of testing, the test device 14 is used to calibrate the pellicle inspection system.

Unlike typical inspection systems for semiconductor wafers in which the detection beam is directed at approximately 90° relative to the semiconductor wafer, increasing the density of raised areas within an array of artificial defects cannot be used as a means for increasing the apparent size of a surface particle to be simulated by a test device. A dense array of raised areas on the test device 14 of FIG. 1 would cause vignetting, i.e. shadowing, of closely adjacent raised areas. This vignetting would occur both with respect to the detection beam from the laser source 10 to the test device 14 and with respect to the escape of light from the test device to the collector 16. The small scanning angle 18 and the small collection angle 22 jeopardize the accuracy of calibrating the optical system using prior art test devices.

Figure 2:
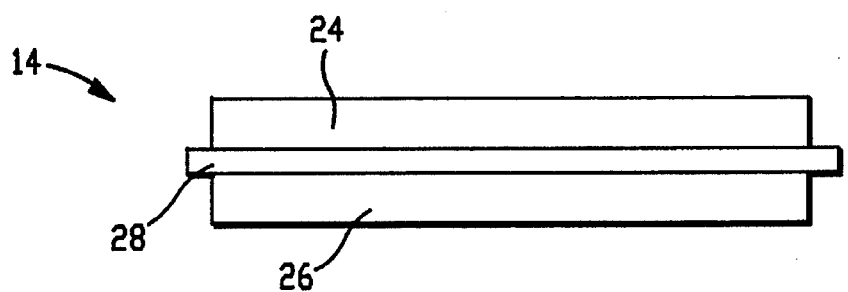
FIG. 2 is a side view of the test device of FIG. 1.
Figure 3:
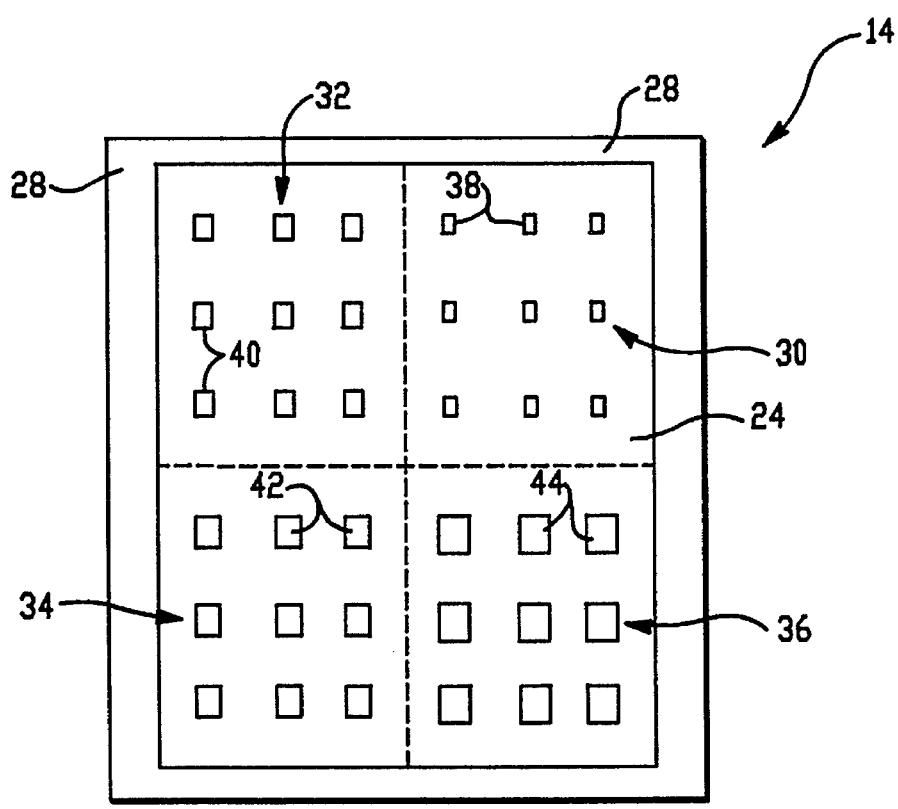
FIG. 3 is a top view of the test device of FIG. 2.

Referring now to FIGS. 1–3, the test device 14 includes upper and lower pellicle-simulating substrates 24 and 26 on opposite sides of a reticle 28. A pellicle is typically a thin membrane used to protect integrated circuit patterns printed on a reticle. Any foreign particles that come to rest on a pellicle are outside the focal plane of a projection lithographic printer, not shown, for printing the integrated circuit patterns. A conventional thickness for a pellicle is approximately 2 micrometers. However, the pellicle-simulating substrates 24 and 26 preferably have a thickness of at least 0.5 millimeters and optimally are 1.0 millimeter or more in thickness. This allows the pellicle-simulating substrates to be handled individually without great concern for the fragility of the substrates. The substrates may be made of a thin glass or a synthetic quartz glass to simulate the optical properties of conventional spin-cast polymer pellicle membranes. Such material can be cleaned often without attacking the material.

The pellicle-simulating substrate on the upper surface of the reticle 28 is mounted to the reticle using a pellicle frame commonly known in the art. However, in calibrating the optical inspection system that includes the laser source 10 and the collector 16, the reticle 28 must be moved downwardly to compensate for the difference between the thickness of the pellicle-simulating substrate 28 and the thickness of a conventional pellicle. That is, the reticle is moved downwardly so that the upper surface of the substrate 24 is placed in the same extrafocal plane that would normally be occupied by the upper surface of a thinner pellicle membrane.

FIG. 3 illustrates four arrays 30, 32, 34 and 36 of diffractors that are used to simulate foreign particles on the upper surface of the pellicle-simulating substrate 24. Arrays of diffractors may also be on the lower surface of the lower pellicle-simulating substrate 26. In contrast to conventional test devices for calibrating surface inspection systems, such as the device described in U.S. Pat. No. 4,512,659 to Galbraith et al., individual diffractors 38, 40, 42 and 44 in the arrays are spaced apart by a greater distance than the diameter of the detection beam of the system to be calibrated. Galbraith et al. teaches that closely spaced, high density light-scattering elements may be used to simulate large particles, while lower density arrays simulate small particles. The diffractors 38, 40, 42, and 44 of FIG. 3, on the other hand, each simulate a single particle. As will be explained more fully below, it is the size of the individual diffractor and the number of vertices that are within the path of a detection beam that determine the apparent size of the diffractors as viewed by the collector. Diffractors 38 in the array 30 are configured to simulate a particle having a size of 15 micrometers. Diffractors 40 simulate a 30 micrometer particle, diffractors 42 simulate a 60 micrometer particle, and diffractors 44 simulate a 120 micrometer particle, While the diffractor arrays 30, 32, 34 and 36 are shown as being in grids of 3×3, typically the diffractors will be arrayed in grids of 9×11. The arrangement is not critical, but adjacent diffractors must be spaced apart by a distance greater than the diameter of a detection beam and should be positioned to prevent vignetting. A typical detection beam diameter is between 100 μm and 1000 μm Adjacent diffractors may be spaced apart by as much as 5 m or more.

As described above, the pellicle-simulating substrate 24 may be made of glass or synthetic quartz glass. The material should be compatible with cleaning chemicals and processes commonly used in the semiconductor industry, thereby allowing periodic cleaning of the substrate without attacking the reliability of the test device. Microlithographic printing techniques can be used to fabricate the diffractors 38, 40, 42, and 44. This permits the diffractors to be precisely located, so that the detection of coordinate locations by a pellicle inspection system can be tested and calibrated. Controlled etching of the substrate determines the location and the height of the diffractors. For example, diffractor heights of 2000 Å to 6000 Å may be provided. Alternatively, diffractors can be fabricated by depositing one or more layers on the substrate.

Figure 4:
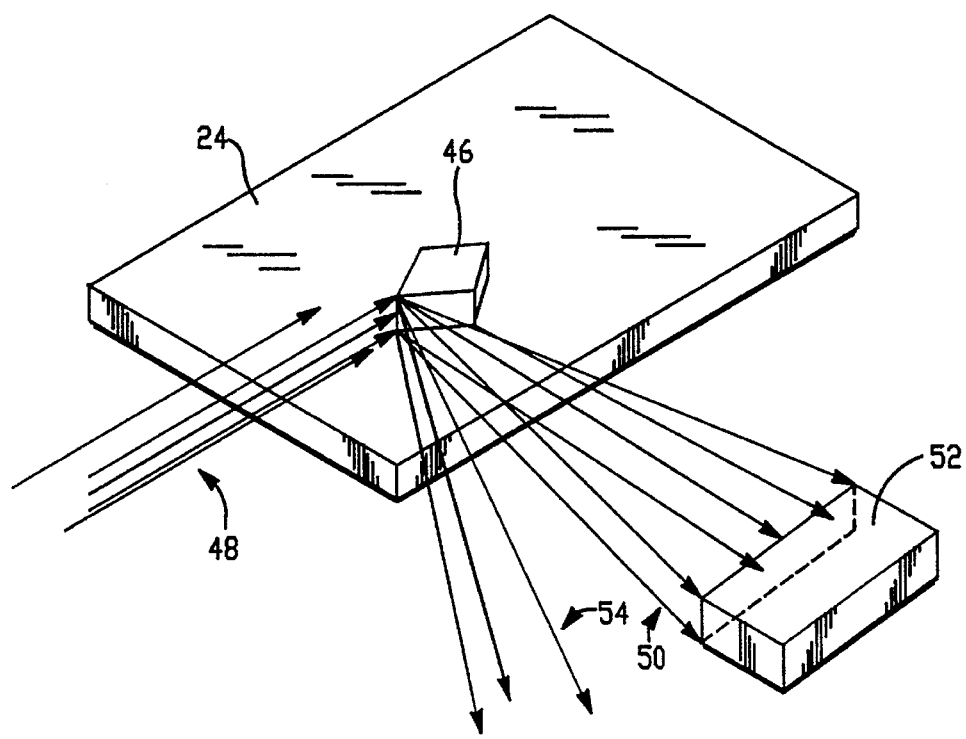
FIG. 4 is a perspective view of the diffraction of a detection beam from a vertex of a diffractor of FIG. 3.

Referring now to FIG. 4, a single diffractor 46 is shown extending above the pellicle-simulating substrate 24. Rays 48 of a detection beam strike a vertex that is aligned to be impinged by a beam having an angle of incidence of 30° or less. The vertex is a beam-diffracting geometric feature. The diffracted light includes rays 50 which are intercepted by a collector 52. Because diffractors are sufficiently spaced apart on the substrate 24, neither the detection beam rays 48 nor the diffracted light rays 50 are intercepted by other diffractors. That is, vignetting does not occur. However, there are light rays 54 that are not received at the collector 52.

The diffractor 46 of FIG. 4 is shown as a polyhedron having a symmetrical configuration with four sidewalls. Any of the vertices that are within the path of a detection beam will diffract light in its unique angular pattern. By increasing the number of vertices, the apparent size of a diffractor, as viewed by the collector 52, can be increased. The apparent size can also be increased by increasing the height of the diffractor 46. Because a single diffractor is used to simulate a single particle, it is not important to have an array of light-scattering elements as described in the prior art patents. Rather, a grid pattern of diffractors, such as a 9×11 grid pattern, is used only as is convenient for the picture element mapping characteristic of an inspection system under calibration.

I claim:

1. A test device for calibrating an optical surface inspection system of the type having a beam source generating a detection beam directed at a surface to be inspected at an oblique angle of incidence of less than 30° relative to the surface and a light collector disposed to detect light scattered from any particles and defects on the surface illuminated by the detection beam, the detection beam having a diameter of a first dimension, the test device substituting for the surface to be inspected for calibration purposes, the test device comprising:

a substrate having a generally planar surface and a plurality of raised diffractors extending from the substrate, the raised diffractors simulating particles and defects on the substrate of at least one size, every diffractor spaced apart from every other diffractor by a distance exceeding the first dimension, such that an obliquely incident detection beam can impinge upon each individual diffractor only one at a time and in an unimpeded manner, each raised diffractor being a single-body member having a configuration of a polyhedron with multiple sidewalls extending upwardly from the generally planar surface of the substrate and at least one vertex defining a beam-diffracting feature of the diffractor, the polyhedron single-body member being characterized by a lateral dimension, a height and the number of vertices, such that each diffractor when illuminated by an obliquely incident detection beam produces an amount of light diffraction detectable in an unimpeded manner by a light collector which corresponds to the lateral dimension, the height and the number of vertices of the polyhedron single-body member forming the diffractor and which also corresponds substantially to the detected amount of light scattered by a particular size of particle or defect simulated by that diffractor.

2. The device of claim 1 wherein the substrate is made of a transparent material.

3. The device of claim 1 wherein the substrate has a thickness greater than 0.5 mm.

4. The device of claim 1 wherein the substrate is coupled to a reticle.

5. The device of claim 1 wherein every diffractor is spaced apart from every other diffractor by a distance of at least 5 mm, such that a detection beam with a diameter of at most 1000 μm and obliquely incident at an angle of at most 5° can impinge each individual diffractor only one at a time and in an unimpeded manner.

6. The device of claim 1 wherein each diffractor has a plurality of vertices disposed such that an obliquely incident detection beam impinges said plurality of vertices in an unimpeded manner.

7. The device of claim 1 wherein the plurality of diffractors are arranged in sets on the substrate that differ from each other in at least one of the lateral dimension, the height and the number of vertices characteristic of the diffractors in each set.

8. A system for calibrating an optical surface inspector, comprising:

a beam source of the optical surface inspector generating a detection beam having a diameter of a first dimension, said detection beam directed along a first beam path, a test substrate having a generally planar surface and a plurality of raised diffractors extending from the substrate, said substrate positioned along said first beam path such that said detection beam is incident upon said substrate at an oblique angle of incidence of less than 30° relative to said surface, every diffractor on said substrate being spaced apart from every other diffractor by a distance exceeding said first dimension, such that said obliquely incident detection beam can impinge upon each individual diffractor only one at a time and in an unimpeded manner from said source along said first beam path to that diffractor on said substrate, each raised diffractor being a single-body member having a configuration of a polyhedron with multiple sidewalls extending upwardly from said generally planar surface of said substrate and at least one vertex defining a beam-diffracting feature of said diffractor, each polyhedron single-body member forming one of said diffractors being characterized by a lateral dimension, a height and the number of vertices impinged upon in an unimpeded manner by said detection beam, and a light collection means of the optical surface inspector disposed relative to said test substrate for detecting light diffracted from a diffractor illuminated by said detection beam, said diffracted light detected by said light collection means following a second unimpeded path from said illuminated diffractor to said light collection means, said light collection means detecting an amount of diffracted light which corresponds to the lateral dimension, the height and the number of vertices of the polyhedron single-body member forming said diffractor illuminated by said detection beam and which also corresponds substantially to an amount of detected light scattered by a particle or defect of a particular size on a surface, said diffractors on said substrate thereby simulating particles and defects of at least one size.

9. The system of claim 8 wherein said detection beam has a diameter of at most 1000 μm.

10. The system of claim 9 wherein said detection beam has an oblique angle of incidence on said substrate of at most 5° relative to said generally planar surface.

11. The system of claim 10 wherein every diffractor is spaced apart from every other diffractor by a distance of at least 5 mm.

12. The system of claim 8 wherein said substrate is made of a transparent material.

13. The system of claim 8 wherein said substrate has a thickness greater than 0.5 mm.

14. The system of claim 8 wherein said substrate is coupled to a reticle.

15. The system of claim 8 wherein each diffractor has a plurality of vertices disposed such that said obliquely incident detection beam impinges said plurality of vertices in an unimpeded manner.

16. The system of claim 8 wherein the plurality of diffractors are arranged in sets on the substrate that differ from each other in at least one of the lateral dimension, the height and the number of vertices characteristic of the diffractors in each set.

* * * * *